| United States Patent [19] | [11] Patent Number: 4,528,299 |
| Uno et al. | [45] Date of Patent: Jul. 9, 1985 |

[54] 1-(2,3-DIMETHYL-4-METHOXYPHENYL)-2-METHYL-3-(1-PYRROLIDINYL)-1-PROPANONE AND ANTI-SPASTIC USE THEREOF

[75] Inventors: Hitoshi Uno, Takatsuki; Tadahiko Karasawa, Toyonaka; Tatsuya Kon, Ashiya; Tsugutaka Ito, Suita, all of Japan

[73] Assignee: Dainippon Pharmaceutical Co., Ltd., Osaka, Japan

[21] Appl. No.: 530,096

[22] Filed: Sep. 7, 1983

[30] Foreign Application Priority Data

Sep. 7, 1982 [JP] Japan ................................. 57-156081

[51] Int. Cl.$^3$ .................... C07D 207/04; A61K 31/40
[52] U.S. Cl. ..................................... 514/428; 548/551
[58] Field of Search .......................... 548/551; 424/274

[56] References Cited

U.S. PATENT DOCUMENTS 3,995,047 11/1976 Morita et al. ....................... 424/267
4,181,803 1/1980 Morita et al. ....................... 546/237
4,277,474 7/1981 Kobda et al. ................... 424/248.57

FOREIGN PATENT DOCUMENTS 0040744 5/1981 European Pat. Off. .

OTHER PUBLICATIONS

Chemical Abstracts, 63, 13290g, (1965).

Primary Examiner—Glennon H. Hollrah
Assistant Examiner—D. B. Springer
Attorney, Agent, or Firm—Wegner & Bretschneider

[57] ABSTRACT 1-(2,3-Dimethyl-4-methoxyphenyl)-2-methyl-3-(1-pyrrolidinyl)-1-propanone and its pharmaceutically acceptable acid addition salts, which are useful as centrally acting muscle relaxants in the treatment of spasticity in mammals including humans, process for the preparation thereof, and pharmaceutical composition containing said compound as an active ingredient.

10 Claims, No Drawings

1-(2,3-DIMETHYL-4-METHOXYPHENYL)-2-METHYL-3-(1-PYRROLIDINYL)-1-PROPANONE AND ANTI-SPASTIC USE THEREOF

The present invention relates to a novel 1-phenyl-2-methyl-3-(1-pyrrolidinyl)-1-propanone derivative which has central muscle relaxant activity and other pharmacological activities and hence is useful as a medicine. More particularly, it relates to 1-(2,3-dimethyl-4-methoxyphenyl)-2-methyl-3-(1-pyrrolidinyl)-1-propanone of the formula:

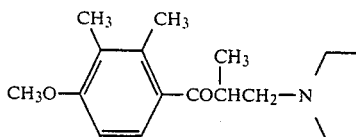

and a pharmaceutically acceptable acid addition salt thereof, a process for the preparation thereof, a method of use of said compound as a medicine, and a pharmaceutical composition containing said compound as an active ingredient.

The pharmaceutically acceptable acid addition salts of the compound (I) include inorganic acid salts such as hydrochloride, hydrobromide, hydroiodide, sulfate, phosphate, etc., and organic acid salts such as formate, acetate, citrate, maleate, fumarate, tartrate, benzoate, lactate, methanesulfonate, etc.

There have hitherto been known various 1-phenyl-3-amino-1-propanone derivatives, for example, the following compounds.

It is known that 2-methyl-1-p-methylphenyl-3-piperidino-1-propanone (generic name: tolperisone) is useful as a centrally acting muscle relaxant [cf. Merck Index, 9th ed., 9219 (1976)]

It is disclosed in U.S. Pat. Nos. 3,995,047 and 4,181,803 that 1-p-$C_{2-3}$ alkylphenyl-2-methyl-3-piperidino-1-propanone shows improved pharmacological activities superior to those of tolperisone.

Japanese Patent Publication No. 11,490/1965 [Chem. Abstr., 63, 13290g (1965)] discloses compounds of the formula:

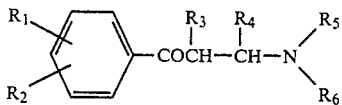

wherein $R_1$ and $R_2$ are the same or different and are each halogen atom or alkyl group, $R_3$ and $R_4$ are the same or different and are each a hydrogen atom or alkyl group, and $R_5$ and $R_6$ are the same or different and are each a hydrogen atom, aliphatic group, or combine together with the adjacent nitrogen atom to form a ring, which have an antispasmodic activity.

Furthermore, U.S. Pat. No. 4,277,474 discloses compounds of the formula:

wherein A is a non-substituted aryl group or aryl group substituted by a hydroxy group, lower alkyl group, lower alkoxy group, aryl group or a halogen, or non-substituted benzo[b]thienyl group or benzo[b]thienyl group substituted by hydroxy group, lower alkyl group, lower alkoxy group, aryl group or halogen, B is a di-lower alkylamino group or heterocyclic group which contains at least one nitrogen atom and may be substituted by a lower alkyl group or aralkyl group; however, when A is p-methylphenyl group, B denotes a group other than piperidino group, and $R_1$ is hydrogen, lower alkyl group or aryl group, or a pharmaceutically acceptable salt thereof, which are useful for treating allergic diseases.

The neurological disorders frequently seen in elderly men are hemiplegia or hemiparesis resulting from cerebral hemorrhage or infarction, muscle spasm, painful shoulder syndromes, low back pain, and the like. These are characterized mainly by hyperreflexia and hypertonia of the muscle, the so-called spasticity. The spasticity also occurs in brain and spinal cord injury and is frequently observed in cerebral palsy, multiple sclerosis and other neuronal disorders. For the treatment of these spastic syndromes, centrally acting muscle relaxants such as tolperisone have been prescribed. However, tolperisone seems to have some drawbacks such as insufficient potency and short duration of actions.

Under the circumstances, the present inventors have intensively studied an improved centrally acting muscle relaxant having potent and prolonged activity. As a result, it has been found that the compound of the formula (I) and a pharmaceutically acceptable acid addition salt thereof show the desired excellent activities.

An object of the present invention is to provide a novel 1-phenyl-2-methyl-3-(1-pyrrolidinyl)-1-propanone derivative which has excellent central muscle relaxant activity. Another object of the invention is to provide a process for the preparation of said compound. A further object of the invention is to provide a pharmaceutical composition containing said compound as an active ingredient which is useful for the treatment of spasticity in mammals including humans. Still further object of the invention is to provide use of said compound for the treatment of spasticity as set forth above. These and other objects and advantages of the invention will be apparent to persons skilled in the art from the following description.

The compound of the formula (I) can be prepared, for example, by reacting 1-(2,3-dimethyl-4-methoxyphenyl)-1-propanone with formaldehyde and pyrrolidine or an acid addition salt thereof. This reaction may be carried out without using any solvent, but is preferably carried out in an appropriate solvent in view of easy operation after the reaction. The solvent includes all solvents which are usually used in a Mannich reaction, for example, lower alcohols (e.g. methanol, ethanol, propanol, isopropanol), aromatic hydrocarbons (e.g. benzene, toluene), ethers (e.g. 1,2-dimethoxyethane), nitroalkanes (e.g. nitromethane), acetonitrile, and a mixture of these solvents. Formaldehyde and pyrrolidine are usually used in an amount of one to about three moles per one mole of 1-(2,3-dimethyl-4-methoxyphenyl)-1-propanone. Formaldehyde may be used in the form of formalin or a polymerized substance such as paraformaldehyde or s-trioxane. The reaction is usually carried out at a temperature of from room temperature to about 130° C. for about 0.5 to 48 hours.

The compound (I) can be isolated from the reaction mixture and purified by conventional methods. According to conditions of the reaction and after-treatment thereof, the compound (I) can be obtained in the form of a free base or an acid addition salt. When the compound (I) is obtained in the form of an acid addition salt, it can easily be converted into a free base by treating it with a base such as an alkali metal carbonate or ammonia in a usual manner. On the other hand, when the compound is obtained in the form of a free base, it can easily be converted into an acid addition salt by treating it with an inorganic or organic acid in a usual manner.

The starting 1-(2,3-dimethyl-4-methoxyphenyl)-1-propanone used in the above reaction is also novel and can be prepared by the method as described in reference example hereinafter.

The pharmacological activities of the compound (I) of the present invention were experimented in comparison with those of known and novel compounds which have a chemical structure similar to that of the present compound (I). The test compounds are shown in Table 1, wherein the compounds 6 to 8 are all novel and are newly prepared by the present inventors.

TABLE 1

| Test compd. | Chemical structure | Note |
|---|---|---|
| A (compd. of the present invention) (Ref. compd.) | CH₃O—⟨2,3-(CH₃)₂C₆H₂⟩—COCH(CH₃)—CH₂—N(piperidine) · HCl | |
| 1 | CH₃—⟨C₆H₄⟩—COCH(CH₃)—CH₂—N(piperidine) · HCl | tolperisone hydrochloride |
| 2 | C₂H₅—⟨C₆H₄⟩—COCH(CH₃)—CH₂—N(piperidine) · HCl | U.S. Pat. Nos. 3995047 and 4181803 |
| 3 | CH₃O—⟨3-CH₃O-C₆H₃⟩—COCH(CH₃)—CH₂—N(piperidine) · HCl | U.S. Pat. No. 4277474 |
| 4 | CH₃—⟨3,5-(CH₃)₂C₆H₂⟩—COCH(CH₃)—CH₂—N(piperidine) · HCl | U.S. Pat. No. 4277474 |
| 5 | CH₃—⟨3-CH₃-C₆H₃⟩—COCH(CH₃)—CH₂—N(piperidine) · HCl | Jap. Pat. Pub. No. 11490/1965 U.S. Pat. No. 4277474 |
| 6 | CH₃O—⟨2,3-(CH₃)₂C₆H₂⟩—COCH(CH₃)—CH₂—N(pyrrolidine) · HCl | Melting point 170–171° C. |
| 7 | CH₃O—⟨2,3-(CH₃)₂C₆H₂⟩—COCH₂CH₂—N(pyrrolidine) · HCl | Melting point 167–172° C. |
| 8 | C₂H₅O—⟨2,3-(CH₃)₂C₆H₂⟩—COCH(CH₃)—N(pyrrolidine) · HCl | Melting point 181–183° C. |

TEST 1

Effect on anemic decerebrate rigidity (α-rigidity)

Anemic decerebrate rigidity is known to be a model showing the abnormal hypertonia. This model was prepared according to the method of Fukuda et al [cf. Japan. J. Pharmacol. 24, 810–813 (1974)]. Male rats of Wistar strain, weighing 250 to 350 g, were used in groups of 5 animals. Under the ether anesthesia, the animal was fixed on its back. After the oesophagus and bilateral common carotid arteries were exposed, the trachea was cannulated and the oesophagus was cut between two placed ligatures. The occipital bone was exposed. The common carotid arteries were ligated bilaterally and a trephined opening was made in the central part of the bone. The dura matter was cut along the basilar artery, and the artery was cauterized with a coagulator of bipolar pincette electrodes (Micro-ID made by Mizuhoika Kogyo Co., Ltd., Japan). After the operation, anesthesia was discontinued. The marked rigidity occurred in the forelimbs within 15 minutes after the operation.

The rat was placed on its back and the hindlimbs fixed. Electromyogram (EMG) was recorded by a coaxial needle electrode inserted into the Musculus triceps brachii of the forelimbs. Reference electrode was inserted into the hindlimb muscle. EMG activities obtained from the muscle were amplified, transformed into the square wave pulses with the window discriminator, and fed into integrator, the out-put of which was amplified and recorded by an inkwriting recorder.

The test compounds were dissolved in distilled water. After the EMG activities had remained stable over 15 to 30 minutes, the test compounds were cumulatively injected at a 5-minute interval into a cannulated femoral vein. The doses administered were 1.25 mg/kg, 2.5 mg/kg, 5.0 mg/kg, 10 mg/kg and finally 20 mg/kg. The EMG activities were expressed as a percentage of the pre-injection value, and the maximal effect within 5 minutes was measured in each dose. The median effective dose ($ED_{50}$), the dose which reduced the EMG activity to 50%, was calculated by the method of Litchfield and Wilcoxon. In addition, the time from disappearance to reappearance of EMG activities after total dose of 20 mg/kg was expressed as the duration of the effect.

TEST 2

Muscle relaxant effect (Traction test)

Traction test was used as an index of the muscle relaxation. Male mice of STD-ddY strain, weighing 20 to 25 g, were used in groups of 5 animals. The test compounds, suspended or dissolved in 0.5% tragacanth solution, were intraperitoneally administered at a volume of 0.1 ml/10 g body weight, and 15 minutes after the administration the muscle relaxant effects were examined according to the method of Courvoisier et al (cf. "Psychotropic Drugs", ed. by Garattini, S. and Ghetti, V., Elsevier Pub. Co., Amsterdam, 1957, page 373). The animal was suspended by their forelimbs on a horizontal metal bar with a diameter of 2 mm. The rod was 18 cm above the floor. The animals which could not put their hindlimb on the rod within 5 seconds were judged as a positive (all-or-nothing way). The median effective dose ($ED_{50}$), the dose which caused the positive effects in 50% of animals, were calculated according to the method of Litchfield and Wilcoxon.

TEST 3

Acute toxicity

Male mice of STD-ddY strain, weighing 23 to 25 g, were used in groups of 10 animals. The test compounds, suspended or dissolved in 0.5% tragacanth solution, were intraperitoneally administered at a volume of 0.1 ml/10 g body weight. After the administration, the mice were kept for 7 days, and observed for death. The median lethal dose ($LD_{50}$), the dose which caused death in 50% of animals, were calculated according to the method of Litchfield and Wilcoxon.

The results of the Tests 1, 2 and 3 are shown in Table 2.

TABLE 2

| Test compound | α-Rigidity reducing effect | | Muscle relaxant effect | Acute toxicity | |
| --- | --- | --- | --- | --- | --- |
| | $ED_{50}$ (mg/kg; i.v.) | Duration (minute) | $ED_{50}$ (mg/kg; i.p.) | $LD_{50}$ (mg/kg; i.p.) | Safety[*1] index |
| A | 2.6 | 16.3 | 68.5 | 160.9 | 2.35 |
| 1 | 12.3 | 0.7 | 156.3 | 210.1 | 1.34 |
| 2 | 12.7 | 2.8 | 64.2 | 128.8 | 2.01 |
| 3 | 20.2 | —[*2] | 158.2 | 246.7 | 1.56 |
| 4 | 6.9 | —[*3] | 122.8 | 156.4 | 1.27 |
| 5 | 15.6 | 8.8 | 59.3 | 139.9 | 2.36 |
| 6 | 7.3 | 11.4 | 77.7 | 145.2 | 1.87 |
| 7 | 17.2 | —[*2] | 87.1 | 174.5 | 2.00 |
| 8 | 9.6 | 14.8 | 75.5 | 134.5 | 1.78 |

[Remarks]:
[*1]($LD_{50}$)/($ED_{50}$ of Muscle relaxant effect)
[*2]Not determined due to incomplete suppression of EMG activity at 20 mg/kg total dose.
[*3]Not determined due to the death of animals.

From the experimental results shown in Table 2, the following points are clear.

(i) The compound of the present invention is about 4.7 times as potent as Compound No. 1 in the reducing activity of α-rigidity and also about 23 times as long as the latter in the duration of action, and further about 2.3 times as potent as the latter in the muscle relaxant activity. The safety index of Compound No. 1 is so low as 1.34, but on the other hand, the compound of the present invention shows such a high safety index as 2.35, which is about 1.8 times that of Compound No. 1.

(ii) The compound of the present invention is about 4.9 times as potent as Compound No. 2 in the reducing activity of α-rigidity and also about 5.8 times as long as the latter in the duration of action.

(iii) The compound of the present invention is about 7.8 and 2.3 times as potent as Compound No. 3 in α-rigidity reducing and muscle relaxant activities, respectively. The safety index of the compound of the present invention is about 1.5 times that of Compound No. 3.

(iv) The compound of the present invention is about 2.7 and 1.8 times a potent as Compound No. 4 in α-rigidity reducing and muscle relaxant activities, respectively.

Compound No. 4 has such a very low safety index as 1.27 and further shows high toxicity in rats.

(v) The compound of the present invention is about 6 times as potent as Compound No. 5 in the reducing activity of α-rigidity and also about 1.9 times as long as the latter in the duration of action.

(vi) The compound of the present invention is about 2.8 times as potent as Compound No. 6, which is merely different from the compound of the present invention in that it has piperidino group instead of 1-pyrrolidinyl group at 3-position, in the reducing activity of α-rigidity and also somewhat longer than the latter in the duration of action. Besides, the compound of the present invention has a higher safety index than that of Compound No. 6.

(vii) The compound of the present invention is about 6.6 times as potent as Compound No. 7, which is merely different from the compound of the present invention in that it has hydrogen atom instead of methyl group at 2-position, in the reducing activity of α-rigidity.

(viii) The compound of the present invention is about 3.7 times as potent as Compound No. 8, which is merely different from the compound of the present invention in that it has ethoxy group instead of methoxy group at paraposition of 1-phenyl group, in the reducing activity of α-rigidity. Besides, the compound of the present invention has a higher safety index than that of Compound No. 8.

Thus, the compound of the present invention has far greater pharmacological activities than known analogous compound Nos. 1 to 5 and has also fairly or far greater pharmacological activities than novel analogous compound Nos. 6 to 8.

As is clear from the above explanation, the compound (I) or its pharmaceutically acceptable acid addition salts have highly improved, excellent central muscle relaxant activities in comparison with the known compounds and also show low toxicity. Accordingly, the compound of the present invention is useful as a centrally acting muscle relaxant for the treatment of the spasticity in mammals including humans which is observed in the diseases such as cerebral hemorrhage or infraction, brain and spinal cord injury, cerebral palsy, multiple sclerosis, trauma, intervertebral disc herniation, painful shoulder syndromes, low back pain, postoperative joint pain, and the like.

The compound (I) and pharmaceutically acceptable acid addition salt thereof can be administered in oral, parenteral or intrarectal route, preferably in oral route. The dose of these compounds varies with the administration routes, the age of the patients, the kinds and severity of the diseases to be treated, or the like, but is in the range of 0.5 to 20 mg, preferably 0.6 to 6 mg, as the free base per kg of body weight per day for humans. The dose may be divided and administered in two to four times per day.

The compound (I) and pharmaceutically acceptable acid addition salts thereof are usually administered to patients in the form of a pharmaceutical composition which contains a non-toxic and effective amount of the compounds. The pharmaceutical composition is usually prepared by admixing the active compound (I) or its salt with conventional pharmaceutical carrier materials which are unreactive with the active compound (I) or its salts. Suitable examples of the carrier materials are lactose, glucose, mannitol, dextran, cyclodextrin, starch, sucrose, magnesium aluminosilicate tetrahydrate, synthetic aluminum silicate, microcrystalline cellulose, sodium carboxymethylcellulose, hydroxypropylstarch, calcium carboxymethylcellulose, ion exchange resin, methylcellulose, gelatin, acacia, hydroxypropylcellulose, low substituted hydroxypropylcellulose, hydroxypropyl methylcellulose, polyvinylpyrrolidone, polyvinyl alcohol, light anhydrous silicic acid, magnesium stearate, talc, tragacanth, bentonite, veegum, carboxyvinyl polymer, titanium dioxide, sorbitan fatty acid ester, sodium lauryl sulfate, cacao butter, glycerin, glycerides of saturated fatty acids, anhydrous lanolin, glycerogelatin, polysorbate, macrogol, vegetable oils, wax, propylene glycol, water, or the like.

The pharmaceutical composition may be in the dosage form of tablets, capsules, granules, fine granules, powders, syrups, suspension, suppositories, injections, or the like. These preparations may be prepared by conventional methods. Liquid preparations may be prepared by dissolving or suspending the active compounds in water or other suitable vehicles, when used. Tablets, granules or fine granules may be coated in a conventional manner.

The pharmaceutical composition may contain as the active ingredient the compound (I) or its pharmaceutically acceptable acid addition salt in the ratio of 0.5% by weight or more, preferably 1 to 70% by weight, based upon the whole weight of the compositions. The composition may further contain one or more other therapeutically active compounds.

The present invention is illustrated more specifically by the following Examples and Reference Examples. It should be understood that the invention is not limited to these examples.

EXAMPLE 1

1-(2,3-Dimethyl-4-methoxyphenyl)-2-methyl-3-(1-pyrrolidinyl)-1-propanone hydrochloride 1-(2,3-Dimethyl-4-methoxyphenyl)-1-propanone (20.0 g), paraformaldehyde (6.2 g) and pyrrolidine (8.9 g) are combined in isopropanol (30 ml) and 35% ethanolic hydrogen chloride (16 ml) is added to adjust the solution to an acidic pH. The mixture is then stirred and heated at reflux for 20 hours. After cooling, acetone (300 ml) is added to the reaction mixture and the resulting solution is cooled in ice water. Crystalline product is filtered and recrystallized twice from ethanol (50 ml)-acetone (50 ml) to give the analytically pure title compound (10.0 g), m.p. 169°–172° C.

Analysis-Calcd. for $C_{17}H_{25}NO_2 \cdot HCl$: C, 65.47; H, 8.40; N, 4.49; Cl, 11.37. Found: C, 65.23; H, 8.43; N, 4.64; Cl, 11.67.

EXAMPLE 2

1-(2,3-Dimethyl-4-methoxyphenyl)-2-methyl-3(1-pyrrolidinyl)-1-propanone and its hydrochloride 1-(2,3-Dimethyl-4-methoxyphenyl)-1-propanone (50.0 g), paraformaldehyde (15.6 g) and pyrrolidine (22.0 g) are combined in acetonitrile (250 ml) and 34% isopropanolic hydrogen chloride (38 ml) is added to adjust the solution to an acidic pH. The mixture is then stirred and heated at reflux for 6.5 hours. After cooling in ice water, crystalline product is filtered and washed with cold acetone. Recrystallization twice from ethanol (150 ml)-acetone (150 ml) gives the analytically pure hydrochloride of the title compound (38.0 g), m.p. 172°–176° C.

Analysis-Calcd. for $C_{17}H_{25}NO_2 \cdot HCl$: C, 65.47; H, 8.40; N, 4.49; Cl, 11.37. Found: C, 65.25; H, 8.25; N, 4.48; Cl, 11.44.

The hydrochloride thus obtained (10.0 g) is added to a solution of potassium carbonate (5.3 g) in water (50 ml) and an oily substance separated is extracted twice with n-hexane (25 ml). The combined n-hexane layers are washed twice with water and dried over anhydrous sodium sulfate. The solvent is distilled off to give the free base of the title compound (7.7 g).

PMR(CDCl$_3$)δ: 1.18 (3H, d, J=7 Hz), 2.18 (3H, s), 2.32 (3H, s), 3.85 (3H, s), 6.71 (1H, d, J=8 Hz), 7.42 (1H, d, J=8 Hz).

REFERENCE EXAMPLE 1-(2,3-Dimethyl-4-methoxyphenyl)-1-propanone

To a stirred solution of 2,3-dimethylanisole (197.0 g) and propionyl chloride (147.0 g) in carbon disulfide (700 ml) is added anhydrous aluminum chloride (232.0 g) at 5°–10° C. over a period of 1.5 hours. Stirring is continued for 2 hours under cooling and additional 3 hours at room temperature. The reaction mixture is poured onto crushed ice—concentrated hydrochloric acid with stirring. The mixture is extracted with chloroform and the chloroform solution is washed successively with water, dilute sodium bicarbonate solution and water and then dried over anhydrous sodium sulfate. After removal of the solvent by evaporation, the residue is distilled at 121°–126° C. (1–2 mmHg) to give the title compound (255.0 g), which is crystallized from n-hexane, m.p. 39°–40° C.

Analysis-Calcd. for $C_{12}H_{16}O_2$: C, 74.97; H, 8.39. Found: C, 74.82; H, 8.36.

PMR(CDCl$_3$)δ: 1.17 (3H, t, J=7 Hz), 2.13 (3H, s), 2.35 (3H, s), 2.87 (2H, q, J=7 Hz), 3.83 (3H, s), 6.73 (1H, d, J=8 Hz), 7.47 (1H, d, J=8 Hz).

| Example 3 | |
|---|---|
| | per 1,000 tablets |
| 1-(2,3-Dimethyl-4-methoxyphenyl)-2-methyl-3-(1-pyrrolidinyl)-1-propanone hydrochloride | 20 g |
| Corn starch | 28 g |
| Lactose | 65 g |
| Microcrystalline cellulose | 30 g |
| Hydroxypropylcellulose | 5 g |
| Light anhydrous silicic acid | 1 g |
| Magnesium stearate | 1 g |

The above components are blended, granulated and made into 1,000 tablets each weighing 150 mg by a conventional method. The tablets are further coated with hydroxypropyl methylcellulose, talc, titanium dioxide, and sorbitan monooleate in a customary manner. There are obtained 1,000 film coated tablets.

| Example 4 | |
|---|---|
| | per 1,000 capsules |
| 1-(2,3-Dimethyl-4-methoxyphenyl)-2-methyl-3-(1-pyrrolidinyl)-1-propane hydrochloride | 50 g |
| Corn starch | 70 g |
| Lactose | 56 g |
| Microcrystalline cellulose | 40 g |
| Talc | 2 g |
| Magnesium stearate | 2 g |

The above components are blended, granulated and filled into 1,000 capsules by a conventional method.

Example 5

| | fine granules |
|---|---|
| 1-(2,3-Dimethyl-4-methoxyphenyl)-2-methyl-3-(1-pyrrolidinyl)-1-propanone hydrochloride | 100 g |
| Corn starch | 200 g |
| Lactose | 660 g |
| Light anhydrous silicic acid | 10 g |
| Hydroxypropylcellulose | 30 g |

The above components are blended and made into fine granules by a conventional method. The fine granules are further coated with dimethylaminoethyl acrylate-methacrylate copolymer, macrogol aand maagnesium stearate.

What is claimed is:

1. 1-(2,3-Dimethyl-4-methoxyphenyl)-2-methyl-3-(1-pyrrolidinyl)-1-propanone or a pharmaceutically acceptable acid addition salt thereof.

2. 1-(2,3-Dimethyl-4-methoxyphenyl)-2-methyl-3-(1-pyrrolidinyl)-1-propanone hydrochloride.

3. A pharmaceutical composition comprising as an active ingredient an effective antispastic amount of 1-(2,3-dimethyl-4-methoxyphenyl)-2-methyl-3-(1-pyrrolidinyl)-1-propanone or a pharmaceutically acceptable acid addition salt thereof in admixture with a pharmaceutically acceptable carrier.

4. The pharmaceutical composition of claim 4 wherein the active ingredient is 1-(2,3-dimethyl-4-methoxyphenyl)-2-methyl-3-(1-pyrrolidinyl)-1-propanone hydrochloride.

5. A method of treating spasticity in mammals which comprises administering to said mammals in need of such treatment an effective antispastic amount of 1-(2,3-dimethyl-4-methoxyphenyl)-2-methyl-3-(1-pyrrolidinyl)-1-propanone or a pharmaceutically acceptable acid addition salt thereof.

6. The method of claim 5 wherein said compound is 1-(2,3-dimethyl-4-methoxyphenyl)-2-methyl-3-(1-pyrrolidinyl)-1-propanone hydrochloride.

7. The method of claim 5 wherein said compound is administered in a daily dosage of from 0.5 to 20 mg per kg of body weight as the free base.

8. The method of claim 7 wherein said compound is 1-(2,3-dimethyl-4-methoxyphenyl)-2-methyl-3-(1-pyrrolidinyl)-1-propanone hydrochloride.

9. The method of claim 7 wherein said daily dosage is in the range of 0.6 to 6 mg per kg of body weight as the free base.

10. The method of claim 9 wherein said compound is 1-(2,3-dimethyl-4-methoxyphenyl)-2-methyl-3-(1-pyrrolidinyl)-1-propanone hydrochloride.

* * * * *